United States Patent
Fagot

(10) Patent No.: US 7,470,438 B1
(45) Date of Patent: Dec. 30, 2008

(54) *ERICACEA* EXTRACTS FOR COMBATING SKIN AGING

(75) Inventor: Dominique Fagot, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/970,797

(22) Filed: Oct. 5, 2001

(30) Foreign Application Priority Data

Oct. 5, 2000 (FR) .................................. 00 12737

(51) Int. Cl.
*A01N 65/00* (2006.01)

(52) U.S. Cl. ...................................... 424/725
(58) Field of Classification Search ............. 424/725
See application file for complete search history.

(56) References Cited

U.S. PATENT DOCUMENTS

| | | | | |
|---|---|---|---|---|
| 3,879,188 A | * | 4/1975 | Fritz et al. | |
| 4,374,661 A | * | 2/1983 | Fritz et al. | |
| 4,569,839 A | * | 2/1986 | Grollier et al. | |
| 4,767,618 A | * | 8/1988 | Grollier et al. | |
| 4,933,177 A | * | 6/1990 | Grollier et al. | |
| 5,320,841 A | * | 6/1994 | Seghizzi et al. | |
| 5,384,123 A | * | 1/1995 | Metsada | |
| PP9,098 P | * | 4/1995 | Milbrath et al. | |
| 5,830,915 A | * | 11/1998 | Pikul et al. | 514/620 |
| 5,876,699 A | | 3/1999 | DiSomma et al. | |
| 7,005,148 B2 | | 2/2006 | Pageon | |

FOREIGN PATENT DOCUMENTS

| | | | |
|---|---|---|---|
| EP | 137811 | * | 4/1985 |
| FR | 2461499 A1 | | 2/1981 |
| FR | 2612775 | * | 9/1988 |
| FR | 2744366 A1 | | 8/1997 |
| HU | 206980 | * | 3/1993 |
| JP | 07309770 A | | 11/1995 |
| JP | 10236940 A | | 9/1998 |
| JP | 2000256176 A | | 9/2000 |
| WO | WO 98/51291 A1 | | 11/1998 |

* cited by examiner

*Primary Examiner*—Michael V Meller
(74) *Attorney, Agent, or Firm*—Buchanan, Ingersoll & Rooney, PC

(57) ABSTRACT

Extracts of plants of the Ericacea family are administered to individuals to combat the signs of aging of the skin, e.g., wrinkles and fine lines, for example by inhibiting the expression of metalloproteases, by inhibiting collagen degradation, or by inhibiting UV-induced skin degradation.

25 Claims, No Drawings

*ERICACEA* EXTRACTS FOR COMBATING SKIN AGING

CROSS-REFERENCE TO PRIORITY APPLICATION

This application claims priority under 35 U.S.C. § 119 of FR-00/12737, filed Oct. 5, 2000, hereby expressly incorporated by reference.

BACKGROUND OF THE INVENTION

1. Technical Field of the Invention

The present invention relates to the administration of at least one extract of at least one plant of the Ericacea family, or composition comprised thereof, for preventively and/or curatively treating the signs of aging of the skin.

This invention especially relates to the administration of such extracts or compositions to inhibit the degradation of the skin and/or mucous membranes by inhibiting collagenases. Too, the present invention relates to a cosmetic regime/regimen for combating aging of the skin and/or mucous membranes.

2. Description of the Prior Art

Human skin consists of two layers or compartments, namely, a surface layer or compartment, the epidermis, and a deep compartment, the dermis.

Natural human epidermis is principally composed of three types of cells: keratinocytes, which form the great majority, melanocytes and Langerhans cells. Each of these cell types contributes, by virtue of its intrinsic functions, towards the essential role played in the body by the skin.

The dermis imparts to the epidermis a solid support. It is also the nourishing factor of the epidermis. It consists mainly of fibroblasts and of an extracellular matrix which is itself composed mainly of collagen, elastin and a substance known as ground substance, these components being synthesized by the fibroblasts. Leukocytes, mastocytes and tissue macrophages are also present therein. It also contains blood vessels and nerve fibers. In normal skin, namely, non-pathological and unscarred skin, the fibroblasts are in the quiescent state, i.e., non-proliferative, metabolically relatively inactive, and immobile.

These collagen fibers provide the dermis with its firmness. Collagen fibers consist of fibrils sealed together, thus forming more than 10 different types of structures. The firmness of the dermis is principally due to the entanglement of the collagen fibers packed together in all directions. The collagen fibers contribute to the elasticity and tonicity of the skin and/or mucous membranes.

The collagen fibers are under constant renewal, but this renewal decreases with age, leading to thinning of the dermis. This thinning of the dermis is also due to pathological causes such as, for example, the hypersecretion of corticoid hormones, certain pathologies or vitamin deficiencies (which is the case for vitamin C in scurvy). It is also accepted that extrinsic factors such as ultraviolet rays, tobacco or certain treatments (glucocorticoids, vitamin D and derivatives, for example) also have an effect on the skin and its collagen content.

However, various factors result in the degradation of collagen, with all of the consequences which may be envisaged on the structure and/or firmness of the skin and/or mucous membranes.

Albeit very strong, collagen fibers are sensitive to certain enzymes known as collagenases. A degradation of collagen fibers promotes the development of flaccid and wrinkled skin, which individuals, preferring the appearance of smooth and taut skin, have universally sought to combat.

Collagenases are part of a family of enzymes designated metalloproteases (MMPs) which are themselves members of a family of proteolytic enzymes (endoproteases) which contain a zinc atom coordinated to 3 cysteine residues and one methionine residue at their active site and which degrade the macromolecular components of the extracellular matrix and of the basal layers at neutral pH (collagen, elastin, etc.). These enzymes, which are very widespread in nature, are present, but poorly expressed in normal physiological phenomena such as the growth of organs and the renewal of tissues.

However, their overexpression in man and their activation are linked to many processes, sometimes pathological, which involve the destruction and remodelling of the matrix. This results in either an uncontrolled resorption of extracellular matrix or, conversely, the installation of a state of fibrosis.

The metalloprotease family consists of several well-defined groups based on their resemblances in terms of structure and substrate specificity (see Woessner J. F., *Faseb Journal*, vol. 5, 2145 (1991)). Among these groups, exemplary are the collagenases for degrading fibrillar collagens (MMP-1 or interstitial collagenase, MMP-8 or neutrophil collagenase and MMP-13 or collagenase 3), gelatinases which degrade type IV collagen or any form of denatured collagen (MMP-2 or gelatinase A (72 kDa), MMP-9 or gelatinase B (92 kDa), stromelysins (MMP-3) whose broad spectrum of activity addresses the proteins of the extracellular matrix such as glycoproteins (fibronectin, laminin), proteoglycans, etc., or, alternatively, membrane metalloproteases.

Prolonged exposure to ultraviolet radiation, particularly to ultraviolet rays of A and/or B type, has the effect of stimulating the expression of collagenases, particularly of MMP-1. This is one of the components of photoinduced aging of the skin.

Moreover, at menopause the principal changes concerning the dermis are a decrease in collagen content and in the thickness of the dermis. In menopausal women, this results in thinning of the skin and/or mucous membranes. Women then experience a sensation of "dry skin" or of taut skin and there is an increase in surface wrinkles and fine lines. The skin presents a rough aspect when touched. Finally, the skin is less supple.

The importance of collagen in the structure of tissues, particularly the skin and/or mucous membranes, and the importance of combating its degradation in order thus to combat aging, whether chronobiological or photoinduced aging and the consequences thereof, the thinning of the dermis and/or the degradation of collagen fibers which result in the development of flaccid and wrinkled skin, may thus be appreciated from the hereinabove description.

SUMMARY OF THE INVENTION

A major object of the present invention is the provision of bioaffecting active agents which elicit an inhibitory effect on collagenases and, to the extent possible, no appreciable side effects.

Thus, it has now surprisingly and unexpectedly been determined that extracts of at least one plant from the Ericacea family exhibit inhibitory activity on collagenase activity.

DETAILED DESCRIPTION OF BEST MODE AND SPECIFIC/PREFERRED EMBODIMENTS OF THE INVENTION

More particularly according to the present invention, the inhibitory activity on the activity of collagenases by an extract of at least one plant from the Ericacea family was to date unknown.

Thus, the present invention features the administration of at least one extract of at least one plant from the Ericacea family, or composition comprised thereof, the extract or the composition being suited for preventively and/or curatively treating the signs of aging of the skin.

By the expression "signs of aging of the skin" is intended any change in the external appearance of the skin due to aging, whether this is chronobiological and/or photoinduced, such as, for example, wrinkles and fine lines, withered skin, flaccid skin, thinned skin, and skin lacking elasticity and/or tonus, and also any internal change in the skin which is not systematically reflected by a changed external appearance, such as, for example, any internal degradation of the skin, particularly of collagen, following exposure to ultraviolet radiation.

This invention also features administration of at least one extract of at least one plant from the Ericacea family, or composition comprised thereof, to inhibit expression of proteases of the extracellular matrix, particularly metalloprotease and even more particularly of type-1 metalloprotease.

This invention also features administration of at least one extract of at least one plant from the Ericacea family, or composition comprised thereof, to treat menopause-related skin complaints/afflictions.

Too, the present invention features administration of at least one extract of at least one plant from the Ericacea family, or composition comprised thereof, to combat skin wrinkles and fine lines.

This invention also features administration of at least one extract of at least one plant from the Ericacea family, or composition comprised thereof, to combat withered skin.

This invention also features administration of at least one extract of at least one plant from the Ericacea family, or composition comprised thereof, to combat flaccid skin.

This invention also features administration of at least one extract of at least one plant from the Ericacea family, or composition comprised thereof, to combat thinned skin.

And the present invention also features administration of at least one extract of at least one plant from the Ericacea family, or composition comprised thereof, to combat a lack of skin elasticity and/or tonus (skin tone).

The Ericacea family comprises about one hundred genera, including, for example, the genera *Erica, Vaccinium, Calluna, Cassiope* and *Rhododendron*.

Thus, the Ericacea extract of the invention is an extract separated from material obtained from at least one plant belonging to a genus selected from among the genera *Erica, Vaccinium, Calluna, Cassiope* and *Rhododendron*.

Preferably according to the invention, the plant belongs to the genus *Vaccinium*.

The genus *Vaccinium* comprises more than 450 species, including the species *Vaccinium myrtillus, Vaccinium angustifollium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccos, Vaccinium stamineum, Vaccinium uliginosum, Vaccinium urceolatum* and *Vaccinium vitis-idaea*.

Thus, the plant extract of the *Vaccinium* genus of the invention is an extract prepared from material obtained from at least one plant belonging to a species selected from among the species *Vaccinium myrtillus, Vaccinium angustifollium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccos, Vaccinium stamineum, Vaccinium uliginosum, Vaccinium urceolatum* and *Vaccinium vitis-idaea*.

Preferably, the plant belongs to the species *Vaccinium angustifollium*.

The extract of at least one plant from the Ericacea family may be any extract separated from any plant material obtained from at least one plant of the Ericacea family.

Accordingly, the extract of at least one plant from the Ericacea family which is administered according to the invention may be obtained from plant material obtained from a whole plant or from a plant part, for example the leaves, the stems, the flowers, the petals, the fruits, the roots or differentiated cells.

By the expression "differentiated plant cells" is intended any plant cell not exhibiting any of the characteristics of a particular specialization, which is capable of surviving by itself rather than being dependent on other cells. These undifferentiated plant cells are potentially capable, under the influence of induction, of any differentiation in accordance with their genome.

Depending on the culture method selected, and in particular depending on the culture medium selected, it is possible to obtain, from the same explant, undifferentiated plant cells with various characteristics.

According to the present invention, the fruits are the preferred.

The extract of at least one plant from the Ericacea family may be any extract prepared from any plant material obtained from at least one plant of the Ericacea family cultured in vivo or obtained via in vitro culturing.

By the expression "in vivo culturing" is intended any culturing of conventional type, namely, in the soil, in the open air or in a greenhouse, or, alternatively, out of the soil.

By the expression "in vitro culturing" is intended the combination of techniques known to this art which makes it possible to artificially obtain a plant or a part of a plant. The selection pressure exerted by the physicochemical conditions during the growth of plant cells in vitro makes it possible to obtain a standardized plant material which is available throughout the year, in contrast with plants cultivated in vivo.

According to the invention, a plant obtained via in vivo culturing is preferred.

Any extraction technique known to this art may be employed to prepare the extract contained in the compositions according to the invention. Particularly exemplary are aqueous and alcoholic extracts, or organic solvent extracts.

By the expression "aqueous solvent" is intended any solvent consisting totally or partially of water. Thus exemplary are water itself, aqueous/alcoholic solvents in any proportion, or solvents comprising water and a compound such as propylene glycol, in any proportion.

Among the alcoholic solvents, particularly exemplary is ethanol.

An extract prepared via the method described in French patent application No. 95/02379 may also be used. This application is assigned to the assignee hereof and is hereby expressly incorporated by reference.

Thus, in a first step, the plant material is ground in a cold aqueous solution. In a second step, the particles in suspension are removed from the aqueous solution obtained from the first step, and, in a third step, the aqueous solution obtained from the second step is sterilized. This aqueous solution corresponds to the extract.

Moreover, the first step may advantageously be replaced with an operation of simple freezing of the plant tissues (for example at −20° C.), followed by an aqueous extraction repeating the second and third steps described above.

Irrespective of the preparation technique according to the invention, subsequent steps for promoting the storage and/or stabilization may be included without, however, modifying the actual nature of the extract. Thus, for example, the extract obtained may be freeze-dried by any conventional freeze-drying method. A powder is thus obtained which can be used directly, or can be mixed in a suitable solvent before use.

According to the invention, an aqueous extract is preferably employed, and, even more preferably, an extract prepared with a solvent composed of water and propylene glycol, such as, for example, Herbasol® marketed by the company COSMETHOCHEM's.

According to the invention, the extract of at least one plant from the Ericacea family may be used alone, or in a mixture of any nature and may be of natural or synthetic origin.

The extract may by itself constitute the active principle for the compositions of the invention.

In particular, the extract of at least one plant from the Ericacea family or composition comprised thereof, is administered by topical application onto the skin and/or the nails and/or the hair.

The amount of extract which is administered according to the invention obviously depends on the desired effect and may thus vary over a wide range.

To provide an order of magnitude, the extract may be administered in pure form in an amount representing from 0.00001% to 20% relative to the total weight of the composition, and preferably in an amount representing from 0.0001% to 10% relative to the total weight of the composition.

The compositions of the invention may be formulated in any pharmaceutical form imaginable, suitable not only for topical application onto the skin and/or mucous membranes and/or the hair, but also for oral administration.

Preferentially, the composition of the invention are formulated for oral administration.

The compositions of the invention may be cosmetic or dermatological compositions. Preferably, according to the invention, the compositions are cosmetic compositions. The composition is a cosmetic composition since it is intended to improve the general appearance of the skin of the individual to whom it is administered.

Most preferably, the compositions of the invention are cosmetic compositions formulated for oral administration.

For oral administration, the compositions of the invention may be in any suitable form, particularly in the form of a drinkable solution, a tablet, a gel capsule, a wafer capsule, or, alternatively, a nutritional food or a nutritional supplement.

Such compositions also comprise at least one suitable excipient for oral administration.

For administration via topical application onto the skin, hair and/or mucous membranes, the compositions according to the invention obviously comprise a cosmetically acceptable support (vehicle, diluent or carrier), namely, a support which is compatible with the skin, mucous membranes, the nails and the hair, and may be in any pharmaceutical form normally employed for topical application, in particular in the form of an aqueous, aqueous/alcoholic or oily solution, an oil-in-water or water-in-oil or multiple emulsion, an aqueous or oily gel, an anhydrous liquid, pasty or solid product, a dispersion of oil in an aqueous phase with the aid of spherules, these spherules optionally being polymer nanoparticles such as nanospheres and nanocapsules, or, preferably, lipid vesicles of ionic and/or nonionic type.

This compositions may be more or less fluid and may present the appearance of a white or colored cream, an ointment, a milk, a lotion, a serum, a paste or a mousse. It may optionally be applied to the skin in the form of an aerosol. It may also be in solid form, for example in the form of a stick. It may be used as a care product, as a cleansing product, as a makeup product or as a simple deodorant product.

In known fashion, the compositions of the invention may contain additives and adjuvants that are conventional in cosmetics and dermatology, such as hydrophilic or lipophilic gelling agents, hydrophilic or lipophilic bioaffecting active agents, preservatives, antioxidants, solvents, fragrances, fillers, UV-screening agents, pigments, colorants, chelating agents, odor absorbers and dyestuffs. The amounts of these various additives and adjuvants are those conventionally employed in the fields under consideration, and range, for example, from 0.01% to 20% relative to the total weight of the composition. Depending on their nature, these additives and adjuvants may be introduced into the fatty phase, into the aqueous-phase, into lipid vesicles and/or into nanoparticles.

When the composition of the invention is an emulsion, the proportion of the fatty phase may range from 5% to 80% by weight and preferably from 5% to 50% relative to the total weight of the composition. The oils, emulsifiers and co-emulsifiers formulated into the composition in emulsion form are selected among those conventionally used in the field under consideration. The emulsifier and co-emulsifier are typically present in the composition in a proportion ranging from 0.3% to 30% by weight and preferably from 0.5% to 20% relative to the total weight of the composition.

Exemplary oils according to the invention include the mineral oils, oils of plant origin (apricot oil or sunflower oil), oils of animal origin, synthetic oils, silicone oils and fluoro oils (perfluoropolyethers). Fatty alcohols (cetyl alcohol), fatty acids and waxes (beeswax) are also exemplary fatty substances.

Exemplary emulsifiers and coemulsifiers according to the invention, include fatty acid esters of polyethylene glycol, such as PEG-40 stearate and PEG-100 stearate, and fatty acid esters of polyols, such as glyceryl stearate and sorbitan tristearate.

And exemplary hydrophilic gelling agents include, in particular, carboxyvinyl polymers (carbomer), acrylic copolymers such as acrylate/alkylacrylate copolymers, polyacrylamides, polysaccharides, natural gums and clays. Exemplary lipophilic gelling agents include modified clays, for instance bentones, metal salts of fatty acids, hydrophobic silica and polyethylenes.

The present invention also features a cosmetic regime or regimen for treating the skin of an individual subject in need of such treatment and which is intended to stimulate collagen synthesis and/or combat age-related and/or menopause-related skin conditions or afflictions and/or to combat thinning of the dermis and/or to combat the development of flaccid and/or wrinkled skin, wherein a cosmetic composition comprising at least one extract of at least one plant of the Ericacea family is topically applied onto the skin, onto the hair and/or onto mucous membranes, or is ingested.

The regime/regimen of the invention is a cosmetic process for improving the aesthetic appearance of the individual.

The cosmetic regime/regimen of the invention may be carried out, in particular, by administering the cosmetic compositions as described above, according to the usual techniques for administering these compositions.

For example: application of creams, gels, sera, lotions, milks, shampoos or antisun/sunscreen compositions onto the skin or onto the hair, or, alternatively, application of toothpaste to the gums and, preferably, by oral administration of a drinkable solution, a tablet, a gel capsule, or a wafer capsule or a nutritional food or a nutritional supplement.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Evaluation of the activity of at least one extract of at least one plant from the Ericacea family on interstitial collagenases:

The effect of an extract of at least one plant from the Ericacea family on the production of interstitial collagenase was evaluated in a model of culture of A2058 cells (obtained from human melanomas: Templeton N. S. et al. 1990; *Cancer Res.*, 50: 5431-5431).

The test extract was that marketed by the company COSMETOCHEM's (Germany), under the trademark Herbasol®.

The A2058 cells were incubated in a DMEM medium containing amino acids at a concentration of 2 mM, sodium pyruvate at a concentration of 1 mM and 10% calf serum. They were then cultured at a density of 50,000 cells per well in 24-well multiwell plates.

Twenty four hours after placing in culture, the cells were contacted with an extract of at least one plant from the Ericacea family. The production of interstitial collagenase was evaluated 48 hours later in the culture medium. This was performed using an ELISA kit (Biotrack human MMP1; Amersham).

The extract of at least one plant from the Ericacea family was tested at concentrations of 0.005%, 0.05% and 0.5%.

The results, expressed as percentages, represent the decrease in the production of interstitial collagenase relative to the control, namely, relative to a culturing carried out under the same conditions in the absence of a plant from the Ericacea family at the concentrations indicated.

These results are reported in the following Table:

TABLE

| Herbasol ® | 0.05% | 0.5% | 5% |
|---|---|---|---|
| % of inhibition | 0% | 7% | 53% |

EXAMPLES 2-11

The following Examples illustrate specific formulations according to the invention. These compositions were formulated by simple intimate admixing of the various components thereof.

EXAMPLE 2

Composition I—soft capsules:

| Excipients: | |
|---|---|
| Soybean oil | 40 mg |
| Wheatgerm oil | 85 mg |
| Soya lecithins | 25 mg |
| Vitamin: | |
| Natural tocopherols | 3 mg |
| Components: | |
| Herbasol ® (extract of *Vaccinium myrtillus*) | 50 mg |

EXAMPLE 3

Composition 2—Shampoo:

| Herbasol (extract of *Vaccinium myrtillus*) | 5.00% |
|---|---|
| Hydroxypropylcellulose (Klucel H ® marketed by Hercules) | 1.00% |
| Fragrance | 0.50% |
| Preservative | 0.30% |
| Water | qs 100.00% |

EXAMPLE 4

Composition 3—Facial care cream (oil-in-water emulsion):

| Herbasol ® (extract of *Vaccinium myrtillus*) | 2.50% |
|---|---|
| Glyceryl stearate | 2.00% |
| Polysorbate 60 (Tween 60 ® marketed by IC) | 1.00% |
| Stearic acid | 1.40% |
| Triethanolamine | 0.70% |
| Carbomer | 0.40% |
| Liquid fraction of karite butter | 12.00% |
| Perhydrosqualene | 12.00% |
| Antioxidant | 0.05% |
| Fragrance | 0.50% |
| Preservative | 0.30% |
| Water | qs 100.00% |

EXAMPLE 5

Composition 4—Gel for the skin:

| Herbasol ® (extract of *Vaccinium myrtillus*) | 1.00% |
|---|---|
| All-trans-retinoic acid | 0.05% |
| Hydroxypropylcellulose (Klucel H ® marketed by Hercules) | 1.00% |
| Antioxidant | 0.05% |
| Isopropanol | 40.00% |
| Preservative | 0.30% |
| Water | qs 100.00% |

EXAMPLE 6

Composition 5—Facial care gel:

| Herbasol ® (extract of *Vaccinium myrtillus*) | 3.00% |
|---|---|
| Hydroxypropylcellulose (Klucel H ® marketed by Hercules) | 1.00% |
| Antioxidant | 0.05% |
| Isopropanol | 40.00% |

EXAMPLE 6-continued

Composition 5—Facial care gel:

| | | |
|---|---|---|
| Preservative | | 0.30% |
| Water | qs | 100.00% |

EXAMPLE 7

Composition 6—Gel:

| | | |
|---|---|---|
| Herbasol ® (extract of *Vaccinium myrtillus*) | | 5.00% |
| Hydroxypropylcellulose (Klucel H ® marketed by Hercules) | | 1.00% |
| Antioxidant | | 0.05% |
| Lidocaine hydrochloride | | 2.00% |
| Isopropanol | | 40.00% |
| Preservative | | 0.30% |
| Water | qs | 100.00% |

EXAMPLE 8

Composition 7—Cream for treating solar erythema (oil-in-water emulsion):

| | | |
|---|---|---|
| Herbasol ® (extract of *Vaccinium myrtillus*) | | 0.50% |
| Glyceryl stearate | | 2.00% |
| Polysorbate 60 (Tween 60 ® marketed by ICI) | | 1.00% |
| Stearic acid | | 1.40% |
| Glycyrrhetinic acid | | 2.00% |
| Triethanolamine | | 0.70% |
| Carbomer | | 0.40% |
| Liquid fraction of karite butter | | 12.00% |
| Sunflower oil | | 10.00% |
| Antioxidant | | 0.05% |
| Fragrance | | 0.50% |
| Preservative | | 0.30% |
| Water | qs | 100.00% |

EXAMPLE 9

Composition 8—Facial anti-wrinkle cream (oil-in-water emulsion):

| | | |
|---|---|---|
| Herbasol ® (extract of *Vaccinium myrtillus*) | | 1.50% |
| Glyceryl stearate | | 2.00% |
| Polysorbate 60 (Tween 60 ® marketed by ICI) | | 1.00% |
| Stearic acid | | 1.40% |
| 5-n-Octanoylsalicylic acid | | 0.50% |
| Triethanolamine | | 0.70% |
| Carbomer | | 0.40% |
| Liquid fraction of karite butter | | 12.00% |
| Perhydrosqualene | | 12.00% |
| Antioxidant | | 0.05% |
| Fragrance | | 0.50% |
| Preservative | | 0.30% |
| Water | qs | 100.00% |

EXAMPLE 10

Composition 9—Lotion:

| | | |
|---|---|---|
| Herbasol ® (extract of *Vaccinium myrtillus*) | | 0.75% |
| Glycolic acid | | 50.00% |
| Hydroxypropylcellulose (Klucel H ® marketed by Hercules) | | 0.05% |
| Preservative | | 0.30% |

EXAMPLE 10-continued

Composition 9—Lotion:

| | | |
|---|---|---|
| NaOH | qs | pH = 2.8 |
| Ethanol | qs | 100.00% |

EXAMPLE 11

Composition 10—Facial cleansing lotion:

| | | |
|---|---|---|
| Herbasol ® (extract of *Vaccinium myrtillus*) | | 0.10% |
| Antioxidant | | 0.05% |
| Isopropanol | | 40.00% |
| Preservative | | 0.30% |
| Water | qs | 100.00% |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for combating cutaneous signs of aging in a menopausal individual in need of such treatment, comprising administering to said individual exhibiting at least one cutaneous sign of aging selected from the group consisting of withered skin, UV-induced internal degradation of the skin, skin wrinkles, fine lines, flaccid skin, thinned skin, lack of skin elasticity and lack of skin tone, wherein said at least one sign of aging is caused by expression of metalloproteases in the extracellular matrix, a composition comprising from 0.00001 to 20% by weight, based on the total weight of the composition, of at least one fruit extract of at least one plant of the Ericacea family selected from the group consisting of *Vaccinium myrtillus, Vaccinium angustifollium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccus, Vaccinium stamineum, Vaccinium uliginosum*, and *Vaccinium urceolatum*, said amount effective to substantially inhibit expression of said metalloproteases in the extracellular matrix of said individual.

2. The method as defined by claim 1, said amount of said at least one extract of at least one plant of the Ericacea family being effective to inhibit the expression of type 1 metalloprotease.

3. The method as defined by claim 1, wherein said cutaneous signs of aging comprise skin wrinkles and fine lines.

4. The method as defined by claim 1, said at least one fruit extract being in a purified state.

5. The method as defined by claim 1, said at least one fruit extract comprising a solution thereof.

6. The method as defined by claim 1, comprising orally administering said at least one fruit extract of at least one plant of the Ericacea family.

7. The method as defined by claim 1, wherein said composition is formulated into a topically applicable, cosmetically/dermatologically acceptable vehicle, diluent or carrier therefore and is administered topically.

8. The method as defined by claim 7, wherein the topically applicable composition is formulated as a cream, ointment, milk, lotion, serum, paste, mousse, makeup, aerosol, deodorant, shampoo, sunscreen, toothpaste, solid or stick.

9. The method as defined by claim 1, wherein said composition is formulated into an orally ingestible, cosmetically/dermatologically acceptable vehicle, diluent or carrier therefore and is administered orally.

10. The method as defined by claim 9, wherein the orally ingestible composition is formulated as a drinkable solution, tablet, capsule, gel, wafer, food, or nutritional supplement.

11. A method for combating cutaneous signs of aging in a menopausal individual in need of such treatment, comprising administering to said individual exhibiting at least one cutaneous sign of aging selected from the group consisting of withered skin, UV-induced internal degradation of the skin, skin wrinkle, fine lines, flaccid skin, thinned skin, lack of skin elasticity and lack of skin tone, wherein said at least one sign of aging is caused by expression of metalloproteases in the extracellular matrix, a composition comprising from 0.0001 to 20% by weight, based on the total weight of the composition, of at least one fruit extract of at least one plant of the Ericacea family selected from the group consisting of *Vaccinium myrtillus, Vaccinium angustifollium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccus, Vaccinium stamineum, Vaccinium uliginosum,* and *Vaccinium urceolatum*, said amount effective to substantially inhibit expression of said metalloproteases in the extracellular matrix of said individual.

12. The method according to claim 11, wherein said composition is formulated into a topically applicable, cosmetically/dermatologically acceptable vehicle, diluent or carrier therefore and is administered topically.

13. The method according to claim 12, wherein the topically applicable composition is formulated as a cream, ointment, milk, lotion, serum, paste, mousse, makeup, aerosol, deodorant, shampoo, sunscreen, toothpaste, solid or stick.

14. The method according to claim 11, wherein said composition is formulated into an orally ingestible, cosmetically/dermatologically acceptable vehicle, diluent or carrier therefore and is administered orally.

15. The method according to claim 14, wherein the orally ingestible composition is formulated as a drinkable solution, tablet, capsule, gel, wafer, food, or nutritional supplement.

16. A method for combating cutaneous signs of aging in a menopausal individual in need of such treatment, comprising administering to said individual exhibiting at least one cutaneous sign of aging selected from the group consisting of withered skin, UV-induced internal degradation of the skin, skin wrinkles, fine lines, flaccid skin, thinned skin, lack of skin elasticity and lack of skin tone, wherein said at least one sign of aging is caused by expression of metalloproteases in the extracellular matrix, a composition comprising from 0.00001% to 20% by weight, based on the total weight of the composition, of at least one fruit extract of at least one plant of the Ericacea family selected from the group consisting of *Vaccinium myrtillus, Vaccinium angustifollium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccus, Vaccinium stamineum, Vaccinium uliginosum,* and *Vaccinium urceolatum*, said amount effective to substantially inhibit expression of said metalloproteases in the extracellular matrix of said individual, said extract being an aqueous, aqueous/alcoholic or aqueous propylene glycol extract, optionally freeze-dried.

17. The method according to claim 16, wherein said composition is formulated into a topically applicable, cosmetically/dermatologically acceptable vehicle, diluent or carrier therefore and is administered topically.

18. The method according to claim 17, wherein the topically applicable composition is formulated as a cream, ointment, milk, lotion, serum, paste, mousse, makeup, aerosol, deodorant, shampoo, sunscreen, toothpaste, solid or stick.

19. The method according to claim 16, wherein said composition is formulated into an orally ingestible, cosmetically/dermatologically acceptable vehicle, diluent or carrier therefore and is administered orally.

20. The method according to claim 19, wherein wherein the orally ingestible composition is formulated as a drinkable solution, tablet, capsule, gel, wafer, food, or nutritional supplement.

21. A method for combating cutaneous signs of aging in a menopausal individual in need of such treatment, comprising administering to said individual exhibiting at least one cutaneous sign of aging selected from the group consisting of withered skin, UV-induced internal degradation of the skin, skin wrinkles, fine lines, flaccid skin, thinned skin, lack of skin elasticity and lack of skin tone, wherein said at least one sign of aging is caused by expression of metalloproteases in the extracellular matrix, a composition comprising from 0.0001 to 20% by weight, based on the total weight of the composition, of at least one fruit extract of at least one plant of the Ericacea family selected from the group consisting of *Vaccinium myrtillus, Vaccinium angustifollium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccus, Vaccinium stamineum, Vaccinium uliginosum,* and *Vaccinium urceolatum*, said amount effective to substantially inhibit expression of said metalloproteases in the extracellular matrix of said individual, said extract being an aqueous, aqueous/alcoholic or aqueous propylene glycol extract, optionally freeze-dried.

22. The method according to claim 21, wherein said composition is formulated into a topically applicable, cosmetically/dermatologically acceptable vehicle, diluent or carrier therefore and is administered topically.

23. The method according to claim 22, wherein wherein the topically applicable composition is formulated as a cream, ointment, milk, lotion, serum, paste, mousse, makeup, aerosol, deodorant, shampoo, sunscreen, toothpaste, solid or stick.

24. The method according to claim 21, wherein said composition is formulated into an orally ingestible, cosmetically/dermatologically acceptable vehicle, diluent or carrier therefore and is administered orally.

25. The method according to claim 24, wherein the orally ingestible composition is formulated as a drinkable solution, tablet, capsule, gel, wafer, food, or nutritional supplement.

* * * * *